United States Patent [19]

Esser et al.

[11] Patent Number: 4,588,736
[45] Date of Patent: May 13, 1986

[54] ANALGESIC 1-ACETONYL-2-(PHENYLIMINO)-IMIDAZOLIDINES AND SALTS THEREOF

[75] Inventors: Franz Esser; Herbert Köppe, both of Ingelheim am Rhein; Wolfgang Abele, Waldalgesheim; Klaus Stockhaus, Bingen am Rhein, all of Fed. Rep. of Germany

[73] Assignee: Boehringer Ingelheim KG, Ingelheim am Rhein, Fed. Rep. of Germany

[21] Appl. No.: 612,340

[22] Filed: May 21, 1984

[30] Foreign Application Priority Data

Jun. 13, 1983 [DE] Fed. Rep. of Germany ....... 3321282

[51] Int. Cl.$^4$ ................... A61K 31/415; C07D 233/50
[52] U.S. Cl. .................... 514/392; 548/315; 548/316
[58] Field of Search .............. 548/315, 316; 424/273 R; 514/392

[56] References Cited

U.S. PATENT DOCUMENTS 4,262,005 4/1981 McCarthy et al. ............. 548/315 X
4,461,904 7/1984 York ..................... 548/315

Primary Examiner—Richard A. Schwartz

Attorney, Agent, or Firm—Hammond & Littell, Weissenberger & Dippert

[57] ABSTRACT

Compounds of the formula

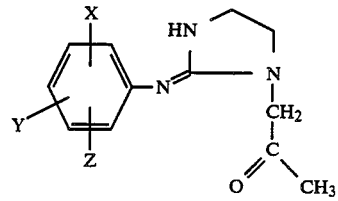

wherein

X, Y and Z are each independently hydrogen, halogen, lower alkyl, halo(lower alkyl), lower alkoxy, halo(lower alkoxy), (lower alkyl)thio or halo(lower alkyl)thio, or Y and Z, together with each other, are lower alkylenedioxy;

and non-toxic, pharmacologically acceptable acid addition salts thereof. The compounds as well as their salts are useful as analgesics.

5 Claims, No Drawings

ANALGESIC 1-ACETONYL-2-(PHENYLIMINO)-IMIDAZOLIDINES AND SALTS THEREOF

This invention relates to novel 1-acetonyl-2-(phenylimino)imidazolidines and non-toxic acid addition salts thereof, to a method of preparing these compounds, to pharmaceutical compositions containing them as active ingredients, and to methods of using them as analgesics.

More particularly, the present invention relates to a novel class of compounds represented by the formula

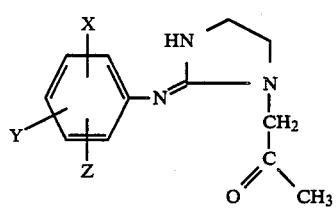

wherein

X, Y and Z are each independently hydrogen, halogen, lower alkyl, halo(lower alkyl), lower alkoxy, halo(lower alkoxy), (lower alkyl)thio or halo(lower alkyl)thio or Y and Z, together with each other, are lower alkylenedioxy; and non-toxic, pharmacologically acceptable acid addition salts thereof.

A preferred subgenus thereunder is constituted by those compounds of the formula I wherein X is fluorine, chlorine, bromine, methyl, methoxy, methylthio, trifluoromethoxy or pentafluoroethoxy, Y is hydrogen, fluorine, chlorine, bromine, methyl or trifluoromethyl, Z is hydrogen, or Y and Z, together with each other, are ethylenedioxy; and non-toxic, pharmacologically acceptable acid addition salts thereof.

The compounds embraced by formula I may be prepared by various methods involving known chemical synthesis principles, among which the following has proved to be particularly suitable:

By hydrating a 1-propargyl-2-(phenylimino)-imidazolidine of the formula

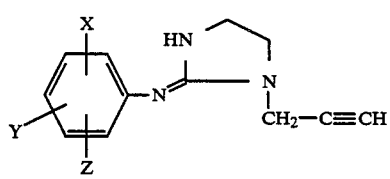

wherein X, Y and Z have the meanings previously defined, or an acid addition salt thereof, in the presence or absence of a heavy metal catalyst.

The reaction is advantageously performed in an aqueous sulfuric acid medium at temperatures between 20° and 100° C., especially at 60° C., preferably in the presence of a mercury (II)salt as the heavy metal catalyst. The reaction product is isolated, after the reaction solution has been made alkaline with 5N sodium hydroxide, by extraction with an organic solvent, preferably ethyl acetate, and subsequent evaporation of the solvent.

The starting compounds of the formula II are described in German Offenlegungsschrift No. 2,523,103. They are obtained by reacting a metal salt of 2-phenylimino-imidazolidine with a propargyl halide.

The compounds embraced by formula I are basic and therefore form addition salts with inorganic or organic acids. Examples of non-toxic, pharmacologically acceptable acid addition salts are those formed with hydrochloric, hydrobromic, sulfuric, phosphoric, nitric, acetic, propionic, butyric, caproic, valeric, oxalic, malonic, tartaric, citric, malic, benzoic, cinnamic, ascorbic, methanesulfonic or ethanesulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

1-Acetonyl-2-(2,4-dichlorophenylimino)-imidazolidine hydrobromide 96 ml of $H_2O$, 3.84 ml of concentrated $H_2SO_4$ and 0.6 g of $HgSO_4$ were added to 21.5 g of 1-propargyl-2-(2,4-dichlorophenylimino)-imidazolidine oxalate (0.06 mol), and the mixture was stirred at 60° C. for 7 hours. Monitoring by thin-layer chromatography indicated complete reaction. The $HgSO_4$ was filtered off, the clear filtrate was diluted with water to 400 ml, made alkaline with 5N NaOH and extracted twice with ethyl acetate. The aqueous phase was discarded. After filtration, the organic phase was dried until a constant weight was obtained, thereby yielding 16.8 g of an oil, corresponding to a crude yield of 97.8%. The 16.8 g of base obtained were dissolved in ethanolic HBr, the solution was filtered and the product was crystallized in the form of the hydrobromide from the filtrate by the addition of ether, then suction-filtered off, washed with ether and dried; 17.0 g of 1-acetonyl-2-(2,4-dichlorophenylimino)imidazolidine hydrobromide were isolated as pure product, corresponding to 77.3% of theory. M.p. 195°–196° C.

EXAMPLE 2

1-Acetonyl-2-(3-fluoro-4-methylphenylimino)-imidazolidine toluene sulfonate

Using the same procedure as in Example 1, but starting from 6.94 g of 1-propargyl-2-(3-fluoro-4-methylphenylimino)imidazolidine, 5.5 g of the title compound were obtained. Yield: 43.5% of theory. M.p. 136°–137° C.

EXAMPLE 3

1-Acetonyl-2-(2-bromo-5-chlorophenylimino)-imidazolidine

Analogous to Example 1, from 6.25 g of 1-propargyl-2-(2-bromo-5-chlorophenylimino)-imidazolidine, 2.0 g of the title compound were obtained as the free base. Yield: 30% of theory. M.p.—(oil).

Thin-layer chromatogram: eluant toluene:dioxan:EtOH:conc.$NH_3$ = 50:40:15:5.

$R_f$-value: 0.65.

EXAMPLE 4

1-Acetonyl-2-(4-chlorophenylimino)-imidazoline hydrobromide

Analogous to Example 1, starting from 6 g of 1-propargyl-2-(4-chlorophenylimino)-imidazolidine, 5.7 g of the title compound were obtained.

Yield: 66% of theory. M.p. 149°–151° C.

EXAMPLE 5

1-Acetonyl-2-(4-chloro-2-methoxyphenylimino)-imidazolidine

Analogous to Example 1, from 5 g of 1-propargyl-2-(4-chloro-2-methoxyphenylimino)-imidazolidine, 2.7 g of the title compound were obtained as the free base.

Yield: 50.4% of theory. M.p. 83°–85° C.

EXAMPLE 6

1-Acetonyl-2-(2-bromo-4,5-ethylenedioxy-phenylimino)-imidazolidine

Analogous to Example 1, 5 g of 1-propargyl-2-(2-bromo4,5-ethylenedioxyphenylimino)-imidazolidine were hydrated to form 4 g of the title compound as the free base.

Yield: 66.4% of theory. M.p. 98°–100° C.

EXAMPLE 7

1-Acetonyl-2-(2-methyl-thio-phenylimino)-imidazolidine

Analogous to Example 1, from 6 g of 1-propargyl-2-(2-methyl-thio-phenylimino)-imidazolidine, 2.2 g of the title compound were obtained as the free base.

Yield: 33% of theory. M.p.—(Oil).

Thin-layer chromatogram: eluant as in Example 3. $R_f$=0.63.

EXAMPLE 8

1-Acetonyl-2-(5-chloro-2-trifluoromethoxy-phenylimino)-imidazolidine

Analogous to Example 1, 1.75 g of 1-propargyl-2-(5-chloro-2-trifluoromethoxy-phenylimino)-imidazolidine were converted into 0.8 g of the title compound as the free base.

Yield: 43% of theory. M.p.—(Oil).

Thin-layer chromatogram: eluant as in Example 3. $R_f$=0.67.

EXAMPLE 9

1-Acetonyl-2-(2-pentafluoroethoxy-5-fluoro-phenylimino)-imidazolidine

Analogous to Example 1, from 3.3 g of 1-propargyl-2-(2-pentafluoroethoxy-5-fluorophenylimino)-imidazolidine, 1.7 g of the title compound were obtained as the free base.

Yield: 49% of theory.

Thin-layer chromatogram: eluant as in Example 1. $R_f$=0.73.

EXAMPLE 10

1-Acetonyl-2-(5-bromo-2-methylphenylimino)-imidazolidine

Analogous to Example 1, from 8.4 g of 1-propargyl-2-(5-bromo-2-methylphenylimino)-imidazolidine, 6.5 g of the title compound were obtained in the form of the free base.

Yield: 72% of theory. M.p. 93°–96° C.

EXAMPLE 11

1-Acetonyl-2-(2-bromo-6-fluorophenylimino)-imidazolidine

Analogous to Example 1, from 2.1 g of 1-propargyl-2-(2-bromo-6-fluorophenylimino)-imidazolidine, 1.2 g of the title compound were obtained as the free base.

Yield: 60% of theory. M.p. 84°–88° C.

EXAMPLE 12

1-Acetonyl-2-(2-chloro-5-trifluoromethylphenylimino)-imidazolidine

Analogous to Example 1, from 5 g of 1-propargyl-2-(2-chloro-5-trifluoromethylphenylimino)-imidazolidine, 2.2 g of the title compound were obtained as the free base.

Yield: 40% of theory. M.p. 93°–95° C.

EXAMPLE 13

1- Acetonyl-2-(2,6-dichlorophenylimino)-imidazolidine

Analogous to Example 1, starting from 6.2 g of 1-propargyl-2-(2,6-dichlorophenylimino)-imidazolidine, 2.1 g of the title compound were obtained.

Yield: 32% of theory. M.p. 84°–86° C.

The compounds of the present invention, that is, those embraced by formula I above and their non-toxic, pharmacologically acceptable acid addition salts, have useful pharmacodynamic properties. More particularly, they exhibit analgesic activity in warm-blooded animals such as mice.

The analgesic effect of the compounds of the present invention was determined by the writhing test in mice after subcutaneous administration. For example, subcutaneous administration of 0.3 mg per kg of 1-acetonyl-2-(2,4-dichlorophenylimino)-imidazolidine hydrobromide, alleviated the pain effect by 50%.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0.0014 to 1.14 mgm/kg body weight, preferably 0.014 to 0.43 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 14

Coated Tablets

The tablet core composition is compounded from the following ingredients:

| | |
|---|---|
| 1-Acetonyl-2-(2,4-dichloro-phenylimino)-imidazolidine hydrobromide | 2.0 parts |
| Lactose | 28.5 parts |
| Corn starch | 17.0 parts |
| Gelatin | 2.0 parts |
| Magnesium stearate | 0.5 parts |

| -continued | |
|---|---|
| Total | 50.0 parts |

Preparation:

A mixture of the active ingredient with lactose and corn starch is granulated with an aqueous 10% gelatin solution through a screen with a mesh size of 1 mm, then dried at 40° C. and passed through a screen once more. The granulate thus obtained is mixed with magnesium stearate and compressed into 50 mg-tablet cores which are coated in the usual way with a thin shell consisting essentially of sugar, titanium dioxide, talc and gum arabic. The finished coated tablets are polished with beeswax. Each tablet contains 2 mg of the active ingredient.

EXAMPLE 15

Tablets

The tablet composition is compounded from the following ingredients:

| | |
|---|---|
| 1-Acetonyl-2-(2,4-dichloro-phenylimino)-imidazolidine hydrobromide | 2.0 parts |
| Lactose | 55.0 parts |
| Corn starch | 38.0 parts |
| Soluble starch | 4.0 parts |
| Magnesium stearate | 1.0 parts |
| Total | 100.0 parts |

Preparation:

A mixture of the active ingredient and magnesium stearate is granulated with an aqueous solution of the soluble starch, the granulate is dried and intimately mixed with lactose and corn starch. The mixture is then compressed into 100 mg-tablets, each containing 2 mg of the active ingredient.

EXAMPLE 16

Suppositories

The suppository composition is compounded from the following ingredients:

| | |
|---|---|
| 1-Acetonyl-2-(2,4-dichloro-phenylimino)-imidazolidine hydrobromide | 1.0 parts |
| Suppository base (e.g. cocoa butter) | 1699.0 parts |
| Total | 1700.0 parts |

Preparation:

The finely powdered active ingredient is stirred into the suppository mass, which has been melted and cooled to 40° C., by means of an immersion homogenizer. At 35° C., 1700 mg-portions of the composition are poured into slightly chilled molds and allowed to harden therein. Each suppository contains 1 mg of the active ingredient.

EXAMPLE 17

Hypodermic Solution

The solution is compounded from the following ingredients:

| | |
|---|---|
| 1-Acetonyl-2-(2,4-dichloro-phenylimino)-imidazolidine hydrobromide | 2.0 parts |
| Sodium chloride | 18.0 parts |
| Distilled water | 2000.0 parts by vol. |

Preparation:

The active ingredient and the sodium chloride are dissolved in the distilled water, the solution is filtered to remove any suspended particles, and the filtrate is filled into 2 cc-ampules under aseptic conditions. Finally, the ampules are sterilized and sealed. Each ampule contains 2 mg of the active ingredient.

Any one of the other compounds embraced by formula I or a non-toxic, pharmacologically acceptable acid addition salt thereof may be substituted for the particular active ingredient in Examples 14 through 17. Likewise, the amount of active ingredient in these illustrative examples may be varied to achieve the dosage unit range set forth above, and the amount and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

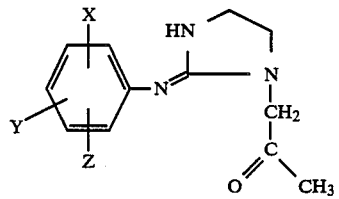

wherein
X, Y and Z are each independently hydrogen, halogen, lower alkyl, perhalogenated lower alkyl, lower alkoxy, perhalogenated lower alkoxy or (lower alkyl)thio, or
Y and Z, together with each other, are lower alkylenedioxy;
or a non-toxic, pharamcologically acceptable acid addition salt thereof.

2. A compound of claim 1
wherein
X is fluorine, chlorine, bromine, methyl, methoxy, methylthio, trifluoromethoxy or pentafluoroethoxy,
Y is hydrogen, fluorine, chlorine, bromine, methyl or trifluoromethyl,
Z is hydrogen, or
Y and Z, together with each other, are ethylenedioxy; or a non-toxic, pharmacologically acceptable acid addition salt thereof.

3. A compound of claim 1, which is 1-acetonyl-2-(2,4-dichloro-phenylimino)-imidazolidine or a non-toxic, pharmacologically acceptable acid addition salt thereof.

4. An analgesic pharmaceutical composition consisting essentially of an inert pharmaceutical carrier and an effective analgesic amount of a compound of claim 1.

5. The method of raising the pain threshold of a warm-blooded animal in need thereof, which comprises perorally, parenterally or rectally administering to said animal an effective amount of a compound of claim 1.

* * * * *